(12) United States Patent
Li et al.

(10) Patent No.: US 8,455,443 B2
(45) Date of Patent: Jun. 4, 2013

(54) METHODS OF USE OF SKIN WOUND HEALING COMPOSITIONS

(75) Inventors: Wei Li, Altadena, CA (US); Mei Chen, Altadena, CA (US); David T. Woodley, Altadena, CA (US); Chieh-Fang Cheng, Alhambra, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 13/484,162

(22) Filed: May 30, 2012

(65) Prior Publication Data

US 2012/0329719 A1 Dec. 27, 2012

Related U.S. Application Data

(63) Continuation of application No. 12/505,361, filed on Jul. 17, 2009, now Pat. No. 8,207,118.

(51) Int. Cl.
*A61K 38/00* (2006.01)
*A61K 45/00* (2006.01)

(52) U.S. Cl.
USPC .......................................... 514/16.5; 424/85.2

(58) Field of Classification Search
None
See application file for complete search history.

(56) References Cited

U.S. PATENT DOCUMENTS

| | | | | |
|---|---|---|---|---|
| 4,857,334 | A | * | 8/1989 | Korol et al. .................... 424/445 |
| 4,929,442 | A | * | 5/1990 | Powell ........................... 424/85.2 |
| 5,070,188 | A | * | 12/1991 | Njieha et al. .................... 530/324 |
| 5,183,805 | A | | 2/1993 | Lee et al. |
| 5,218,093 | A | | 6/1993 | Guo et al. |
| 5,599,788 | A | | 2/1997 | Purchio et al. |
| 6,475,490 | B1 | | 11/2002 | Srivastava et al. |
| 7,081,240 | B1 | | 7/2006 | Akella et al. |
| 8,022,037 | B2 | | 9/2011 | Li et al. |
| 8,207,118 | B2 | | 6/2012 | Li et al. |
| 2001/0034042 | A1 | | 10/2001 | Srivastava |
| 2007/0098735 | A1 | | 5/2007 | Chandawarkar |
| 2009/0005317 | A1 | | 1/2009 | Nishida et al. |
| 2009/0305973 | A1 | | 12/2009 | Kim et al. |
| 2010/0035815 | A1 | | 2/2010 | Li et al. |
| 2011/0301090 | A1 | | 12/2011 | Li et al. |

FOREIGN PATENT DOCUMENTS

| | | |
|---|---|---|
| WO | 9203476 A1 | 3/1992 |
| WO | 2008086358 A1 | 7/2008 |
| WO | 2012060832 A1 | 5/2012 |

OTHER PUBLICATIONS

Cheng, C.-F. et al. 2008. Transforming Growth Factor alpha (TGFalpha)-Stimulated Secretion of HSP90alpha: Using the Receptor LRP-1/CD91 to Promote Human Skin Cell Migration against a TGFbeta-Rich Environment during Wound Healing. Molecular and Cellular Biology, May 2008, vol. 28, No. 10, pp. 3344-3358.
Cheng, C.F. et al. 2008. Secretion of Heat Shock Protection-90 (Hsp90) by Normal Cells Under Stress or by Tumor Cells during Invasion: Why? Cancer Therapy, vol. 6, 765-772, pp. 765-772.
Genbank X 15183, Jan. 30, 1995, Human mRNA for 90-kDa heat-shock protein.
Li, W et al. Extracellular heat shock protein-90alpha: linking hypoxia to skin cell motility and wound healing. The EMBO Journal (2007) 26, pp. 1221-1233.
Nemoto T. et al. 1998. Oligomeric forms of the 90-kDa heat shock protein. Biochem J. vol. 330, pp. 989-995.
Woodley, D.Y. et al. Participation of the lipoprotein receptor LRP1 in hypoxia-HSP9Oalpha autocrine signaling to promote keratinocyte migration. Journal of Cell Science 122, (2009), pp. 1495-1498.

* cited by examiner

*Primary Examiner* — Marianne P Allen
(74) *Attorney, Agent, or Firm* — McDermott Will & Emery LLP

(57) ABSTRACT

A wound healing composition comprising a class of polypeptide compounds having a polypeptide chain with 5 to 120 amino acid units per chain. The composition includes a pharmaceutical medium to carry the polypeptide compound, such as an aqueous solution, suspension, dispersion, salve, ointment, gel, cream, lotion, spray or paste. Additionally, a method of applying a wound healing composition comprising a class of polypeptide compounds having a polypeptide chain with 5 to 120 amino acid units per chain in a concentration of from about 1 µg/ml to about 100 µg/ml for a time sufficient to heal the wound is disclosed.

15 Claims, 3 Drawing Sheets

Day 4

Day 6

Day 8

Day 11

Day 13

Day 15

Control (left) vs. F-3 fragment of Hsp90 (right) (one treatment with 300 µg)

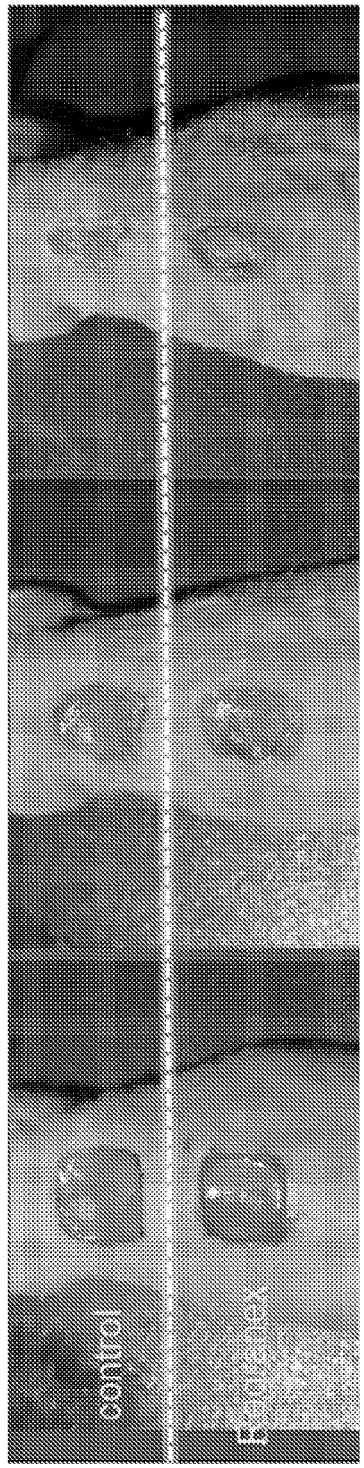
FIG. 3A Day 0
FIG. 3B Day 5
FIG. 3C Day 7
FDA-Approved Regranex (PDGF-BB, at recommended 40 μg) showed little effect
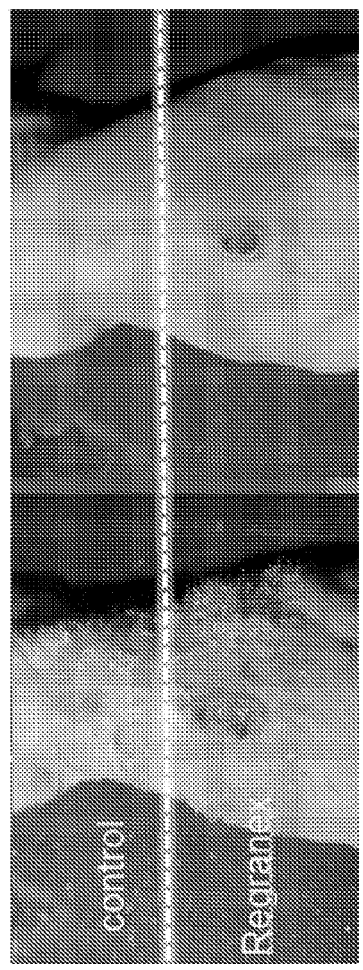
FIG. 3D Day 10
FIG. 3E Day 12

METHODS OF USE OF SKIN WOUND HEALING COMPOSITIONS

CROSS-REFERENCE TO RELATED APPLICATIONS

This application is a continuation application of U.S. patent application Ser. No. 12/505,361, entitled "Skin Wound Healing Compositions and Methods of Use Thereof," filed Jul. 17, 2009, (now U.S. Pat. No. 8,207,118, issued Jun. 26, 2012), the entire content of which is incorporated herein by reference.

STATEMENT REGARDING FEDERALLY SPONSORED RESEARCH

This invention was made with government support under Grant Nos. GM67100 and AR46538 awarded by the National Institutes of Health. The government has certain rights in the invention.

BACKGROUND

1. Field of the Disclosure

This disclosure resides in the field of wound healing compositions and use thereof. Particularly, this disclosure relates to compositions of polypeptides and the topical application of these compositions to the skin to expedite wound healing by promoting all skin cell migration.

2. Description of the Related Art

Wound healing, or wound repair, is an intricate process in which the skin repairs itself after injury. In normal skin, the epidermis (outermost layer) and dermis (inner or deeper layer) exists in a steady-stated equilibrium, forming a protective barrier against the external environment. The normal wound healing process can be broadly classified into three stages namely the inflammatory, proliferative and maturation phases. The inflammatory phase lasts 0-2 days and involves an orderly recruitment of cells to the wound area. This is followed by the 2-6 day proliferative phase, in which fibroblasts, keratinocytes and other cells in the wound bed begin to actively proliferate to close the wound. During the first phase of tissue repair, an acute inflammatory response with cellular migration occurs. Neutrophils predominate for the first 24-48 hours; macrophages become active by the third day. The neutrophils and macrophages phagocytose and digest pathologic organisms and tissue debris. The maturation phase follows the proliferative phase, peaking at 21 days, by which time the wound is completely healed by restructuring the initial scar tissue.

A problematic wound does not follow the normal time table for the healing process as described above. The increased time required for a problematic wound can cause unwanted cost and pain associated with the slowed healing, as well as a decrease in job production and overall quality of life. Among the two million people diagnosed yearly with pressure ulcers, 900,000 have non-healing lower extremity ulcers. It is estimated that 18% of patients with diabetes over the age of 65 will have chronic, non-healing foot ulcers. Moreover, 50,000 lower extremity amputations are performed each year due to infected lower leg chronic wounds. The quality of life due to morbidity of non-healing leg ulcers is significantly compromised because of wound odor, infection, and pain. In addition, these issues also lead to social isolation and diminished self-image in patients with chronic skin wounds. Financially, the cost for managing delayed wound healing in the US elderly is estimated at $9 billion per year.

A great deal of time and expense has been utilized in the field of chronic wound healing. Akella et al. discloses in U.S. Pat. No. 7,081,240, the use of a protein mixture for treating wounds, wherein the mixture is isolated from bone or produced from recombinant proteins such as bone morphogenetic proteins, transforming growth factors and fibroblast growth factors. However, the overall clinical outcomes of growth factor therapy have been disappointing and few growth factors have ultimately received FDA approval.

Kiss discusses the use of non-growth factor proteins for use in wound healing comprised of human alpha1-antitrypsin, human placental alkaline phosphatase, human transferring and $\alpha_1$-acid glycoprotein. However, this method's draw back is that it requires the complicated sequential application of several agents that act at different steps, and also may require adjustment of the compositions according to each treatment. Similarly, the use of skin substitutes has not been cost-effective.

Re-epithelialization is a critical event in human skin wound healing, in which epidermal keratinocytes laterally migrate to close a wound. In chronic wounds, keratinocyte migration is blocked and the wounds remain open, causing patient morbidity and even fatality.

During human skin wound healing, a critical rate-limiting step is the initiation of the resident epidermal and dermal cells at the wound edge to migrate into the wound bed. Human keratinocytes (HKCs) laterally migrate across the wound bed from the cut edge to eventually close the wound, the process known as re-epithelialization. The dermal cells, including dermal fibroblasts (DFs) and dermal microvascular endothelial cells (HDMECs), start to move into the wound following the HKC migration, where these cells deposit matrix proteins, contract and remodel the newly closed wound and build new blood vessels. HKC migration is largely driven by TGFα in human serum and is not affected by high concentrations of TGFβ family cytokines co-present in human serum. In contrast, the presence of TGFβ blocks the dermal cell migration even in the presence of their growth factors, such as PDGF-BB and VEGF. Therefore, while it is understandable why HKC migration jumpstarts ahead of DF and HDMEC migration during wound healing, it has remained as a puzzle how DFs and HDMECs move into the wound bed in the presence of abundant TGFβ.

Other research has involved the use of heat shock protein to promote wound healing. For example, Srivastava et al. discloses in U.S. Pat. No. 6,475,490 compositions comprising heat shock proteins, including gp96, hsp90, and hsp70, uncomplexed or complexed noncovalently with antigenic molecules. However, the use of the entire length of these large molecules in pharmaceutical compositions results a reduced efficacy per unit weight of the protein.

SUMMARY

In order to overcome the above mentioned problems, this disclosure identifies a wound healing composition comprising a class of polypeptide compounds having a polypeptide chain of relatively low size. In one embodiment of the present disclosure, the polypeptide chain has 5 to 120 amino acid units per chain. Optionally, the composition includes a pharmaceutical medium to carry the polypeptide compound, such as an aqueous solution, suspension, dispersion, salve, ointment, gel, cream, lotion, spray or paste.

In another embodiment of the present disclosure, the polypeptide chain has from 20 to 60 amino acid units per chain. Optionally, the polypeptide chain comprises the amino acid sequences of hsp90α peptide from amino acids 236 to 350, SEQ ID NO:1: EEKEDKEEEKEKEEKESEDK-
PEIEDVGSDEEEEKKDGDKKKKKKIKEKYIDQEE, or
SEQ ID NO: 2: SDEEEEKKDGDKKKKKKIKEKY-
IDQEE. Optionally, the composition can comprise a mixture
of polypeptide chains of from 5 to 120 amino acid units,
20-60 amino acid units or the specific amino acid units shown
above.

The present disclosure is also directed to a method of
healing a skin wound comprising contacting a first effective
amount of a pharmaceutical composition consisting of a
polypeptide compound having a polypeptide chain to the skin
wound. The polypeptide chain is from 5 to 120 amino acid
units per chain, 20 to 60 amino acid units per chain, or com-
prises the amino acid sequences of hsp90α peptide from
amino acids 236 to 350, SEQ ID NO: 1: EEKEDKEEEKE-
KEEKESEDKPEIEDVGSDEEEEKKDGD-
KKKKKKIKEKYIDQEE, or SEQ ID NO: 1:
SDEEEEKKDGDKKKKKKIKEKYIDQEE.

The method optionally uses a pharmaceutical composition
having a pharmaceutical medium to carry the polypeptide
compound, consisting of an aqueous solution, suspension,
dispersion, salve, ointment, gel, cream, lotion, spray or paste.

In another embodiment, the polypeptide compound is for-
mulated in a concentration of from about 10 µg/ml to about 3
mg/ml in said pharmaceutical medium. Optionally, the
polypeptide compound is formulated in a concentration of
from about 30 µg/ml to about 500 µg/ml in said pharmaceu-
tical medium.

In one embodiment of the method of wound healing, the
composition is applied to the wound about every 6 to about
every 72 hours. Optionally, the composition is applied to the
wound about every 24 to about every 48 hours.

Additional advantages and other features of the present
disclosure will be set forth in part in the description which
follows and in part will become apparent to those having
ordinary skill in the art upon examination of the following or
may be learned from the practice of the disclosure. The
advantages of the disclosure may be realized and obtained as
particularly pointed out in the appended claims.

As will be realized, the present disclosure is capable of
other and different embodiments, and its several details are
capable of modifications in various obvious respects, all with-
out departing from the disclosure. Accordingly, the drawings
and description are to be regarded as illustrative in nature, and
not as restrictive.

BRIEF DESCRIPTION OF THE DRAWINGS

FIGS. 3A-3E are pictures of the results of skin wound
healing of mice comparing an FDA approved compound (Re-
granex™, PDGF-BB) vs a control cream.

DETAILED DESCRIPTION OF ILLUSTRATIVE
EMBODIMENTS

Not to be bound by theory, it is believed that following skin
injury, paracrine- or autocrine-released TGFα stimulates
membrane translocation and secretion of pre-existing hsp90α
proteins in HKCs. The secreted hsp90α jumpstarts HKC
migration, a critical event of re-epithelialization process, by
binding to the CD91/LRP-1 receptor on the cell surface.
When extracellular hsp90α defuses into and reached certain
concentration in the wound bed, it starts to induce migration
of DFs and HDMECs from the cut edge into the wound bed
even under "hazard" conditions: no ATP and ATPase activity
and in presence of general cell motility inhibitors, such as
TGFβ family cytokines. Thus, extracellular hsp90α is uti-
lized for skin wound healing. However, when chronic wounds
are present, the skin is unable to produce hsp90α for wound
healing. Thus, an additive to promote skin wound healing
must be applied to the wound.

Figure 1:
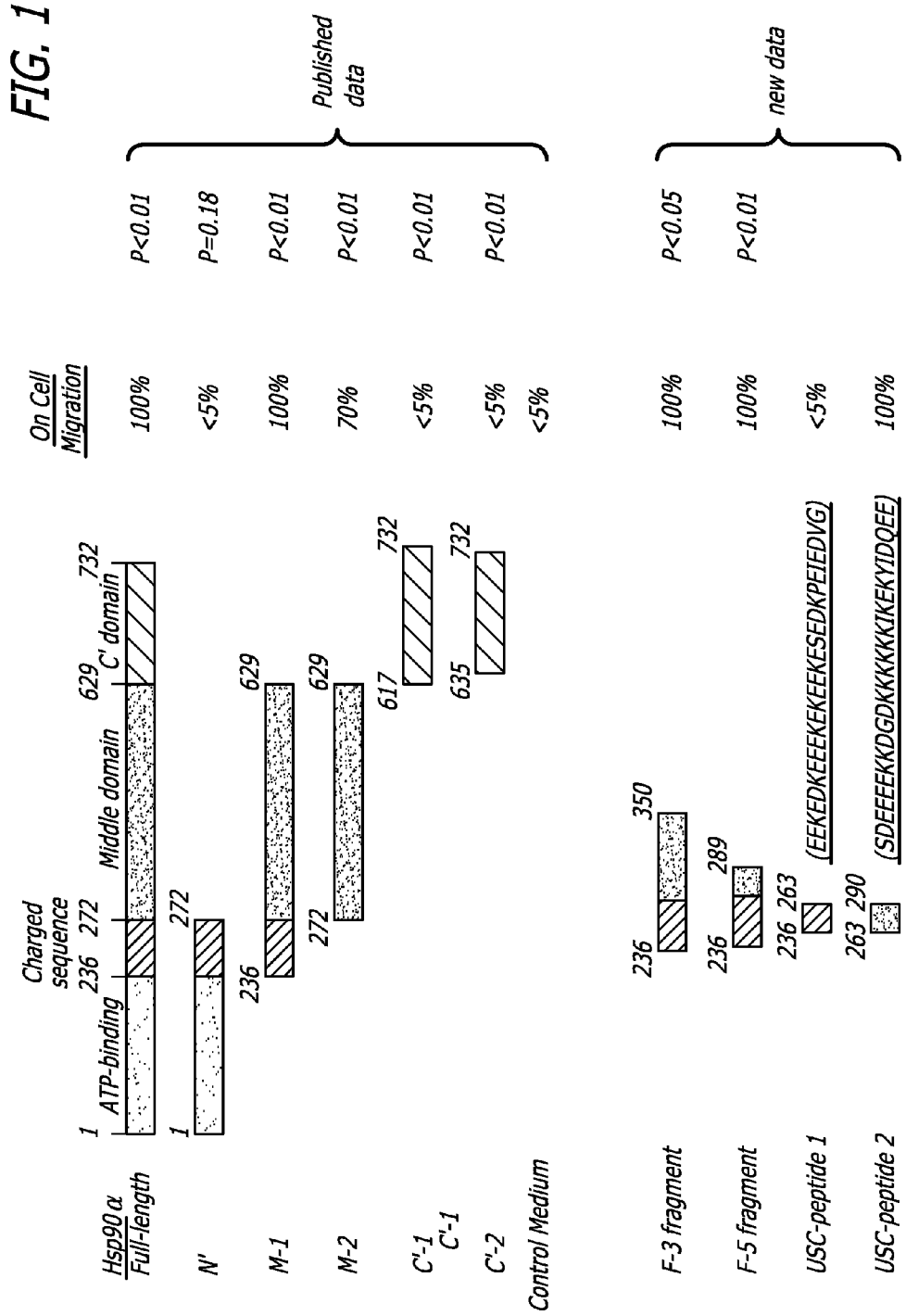
FIG. 1 is a bar graph showing various efficacies of polypep-
tide compounds and their effects on wound healing in mice as
compared to a control cream.
Figure 2A:
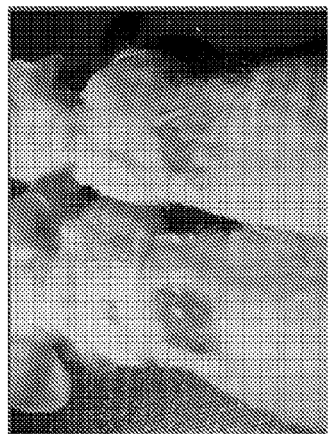
FIGS. 2a-f are pictures of the results of skin wound healing
of mice comparing a polypeptide having a peptide chain with
115 amino acids vs a control cream.
Figure 2B:
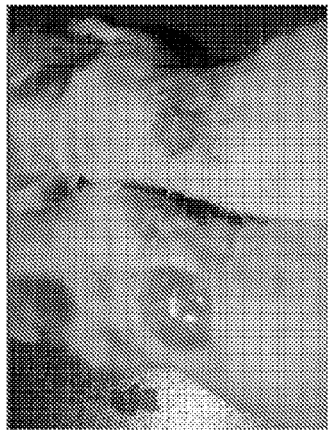
Figure 2C:
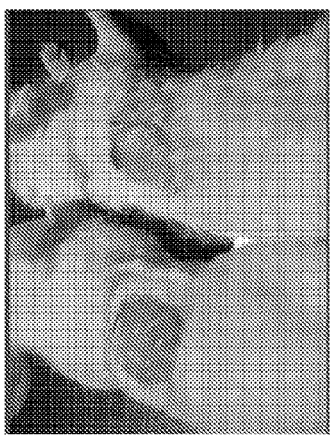
Figure 2D:
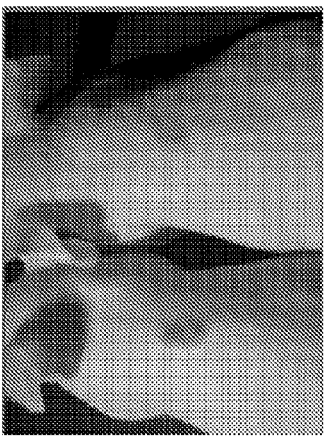
Figure 2E:
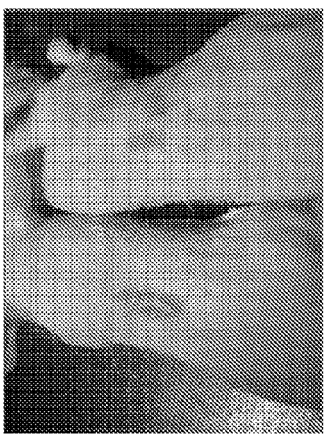
Figure 2F:
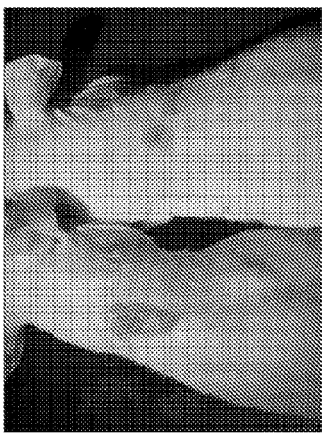

FIG. 1 contains a list of amino acid sequences that were
tested for in vitro efficacy as compared to a control medium.
The amino acid sequences are identified in FIG. 1 as follows:

```
F-5 fragment: (SEQ ID NO: 1):
EEKEDKEEEKEKEEKESEDKPEIEDVGSDEEEEKKDGDKKKKKKIKEKYI
DQEE USC-peptide 2: (SEQ ID NO: 2):
SDEEEEKKDGDKKKKKKIKEKYIDQEE
```

As can be seen in FIG. 1, the full-length (WT) hsp90α
showed a remarkable pro-motility activity, in comparison to
the control medium. The middle domain plus the charged
sequence (M-1) show a similar degree of the activity as the
WT hsp90α. However, the middle domain lacking the
charged sequence showed a significantly decreased activity
(M-2), although the charged sequence plus the entire N'-ter-
minal domain (N') showed no stimulating activity. The two
C'-terminal domains (C'-1 and C'-2, made to ensure the
results) both showed a moderate pro-motility activity. There-
fore, hsp90α promotes HKC migration mainly through its
middle and the carboxyl domains, consistent with their sur-
face location in hsp90α. Accordingly, a composition com-
prising the middle domain of hsp90α would exhibit similar
wound healing properties as that of a composition comprising
hsp90α alone.

However, as can also be seen in FIG. 1, not all of the full
hsp90α protein or the entire middle domain and charged
portion of hsp90α protein is necessary to promote wound
healing. The F-3 fragment consisting of 115 amino acid units
which is from amino acid number 236 to 350 and the F-5
fragment having 54 amino acid units from amino acid number
236 to 289 (SEQ ID NO: 1 EEKEDKEEEKEKEEKESED-
KPEIEDVGS DEEEEKKDGDKKKKKKIKEKYIDQEE)
exhibit similar activity as that of full length hsp90α, that
being 100% on cell migration. Thus, the unnecessary portions
of hsp90α need not be included in a composition for wound
healing, thereby allowing a composition to be more effica-
cious per weight of active wound healing agent. Moreover,
instead of relying on complicated isolation and extraction
methods to obtain the hsp90α protein or the middle domain
plus charged portion of hsp90α protein, more inexpensive
and conventional methods of synthesis may be employed to
obtain the lower chain length polypeptide chains.

To prove the efficacy of polypeptide compounds of 115
amino acid units and 54 amino acid units were synthesized via
convention means. 100 µg F-3 fragments in 100 µl of 10%
Carboxymethylcellulose cream and the cream alone was topi-
cally applied to the 1 cm×1 cm wound on the back of nude
mice daily for 5 days, and wounds were analyzed every two
days. Selected wound images of a representative experiment
are shown in FIGS. 2A-2F. It can be seen that F-3 significantly
accelerated closure of the wounds beginning on day 4, day 6,
day 8, day 11, day 13 and day 15 as compared to the cream
control.

EXAMPLE

In the example below, the following conditions or methods
were utilized.

The pharmaceutical 100 µl of 10% carboxymethylcellu-
lose cream (Sterile) is mixed in and the 1 cm×1 cm wound on the back of a nude mouse is topically covered. Following this treatment, the wound is covered with a few antibiotics and bandi and the bandi are fixed by rolling the mouse with coban. The F-3 compound mixture is then added every day for up to five days and the wound is analyzed every two days.

To prepare mice for topical treatment of F-3, 1.0-cm×1.0-cm full-thickness excision wounds were made by lifting the skin with forceps and removing full thickness skin with a pair of scissors on the mid-back of 8 to 10 week old mice. The wounds were topically covered by 100 µl 10% carboxymethylcellulose either without (as a control) or with 300 µg recombinant F-3 compound. The wound area was then covered with Band-Aid and Coban, a self-adherent wrap, to prevent desiccation. Only one dose of F-3 compounds was administered to the wound. To measure the wound area, standardized digital photographs were taken of the wounds at 4, 6, 8, 11, 13 and 15 days post-wounding and the open wound areas were determined with an image analyzer (AlphaEase FC version 4.1.0, Alpha Innotech Corporation). Percentage of wound area was defined by comparing areas of healing wounds to those of the original wounds. The Student T test was used for the statistical analysis. All animal studies were conducted using protocols approved by the University of Southern California Institutional Animal Use Committee.

The following example is offered for purposes of illustration and are not intended to limit the scope of the invention.

A 1.0-cm$^2$ (1cm×1cm) square full-thickness excision wound was made on the mid-back of 8 to 10 week old athymic nude mice and the pharmaceutical composition of F-3 was applied topically daily for 5 days (n=10 mice per group). (A) Representative day 4, 6, 8, 11, 13 and 15 wounds are shown. Wound sizes were significantly reduced in mice topically treated with the cream containing F-3 (right panels), but not cream alone (left panels). (B) Mean±SD wound size measurements at day 4, 6, 8, 11, 13 and 15 post-wounding (n=10 mice for each group).

To compare efficacy of the F-3 compound, a study using FDA approved Regenerex™ was conducted. Using the above methods, a 40 µg dose of PDGF-BB (Regenerex™) was applied to mice for 5 days (n=10 mice per group) vs F-3 compound. (A) Representative day 0, 5, 7, 10 and 12 wounds are shown in FIGS. 3A-3E. As can be seen from the figures, wound sizes were significantly reduced in mice topically treated with the cream containing F-3 (upper panels), but not Regenerex™ (lower panels).

The present disclosure can be practiced by employing conventional materials, methodology and equipment. Accordingly, the details of such materials, equipment and methodology are not set forth herein in detail. In the previous descriptions, numerous specific details are set forth, such as specific materials, structures, chemicals, processes, etc., in order to provide a thorough understanding of the disclosure. However, it should be recognized that the present disclosure can be practiced without resorting to the details specifically set forth. In other instances, well known processing structures have not been described in detail, in order not to unnecessarily obscure the present disclosure.

Only a few examples of the present disclosure are shown and described herein. It is to be understood that the disclosure is capable of use in various other combinations and environments and is capable of changes or modifications within the scope of the inventive concepts as expressed herein.

The Sequence listing in "SEQUENCE LISTING.TXT" created on Mar. 22, 2011, being 1.04 KB in size is incorporated by reference.

The invention claimed is:

1. A method of healing a skin wound comprising contacting the skin wound with an effective amount of a pharmaceutical composition comprising a polypeptide, wherein the polypeptide consists of amino acid sequence EEKEDKEEEKEKEEKESEDKPEIEDVGS-DEEEEKKDGDKKKKKKIKEKYIDQEE (SEQ ID NO: 1).

2. The method of healing a skin wound according to claim 1, wherein the pharmaceutical composition further comprises a pharmaceutical medium to carry the polypeptide, wherein the pharmaceutical medium is selected from the group consisting of an aqueous solution, suspension, dispersion, salve, ointment, gel, cream, lotion, spray or paste.

3. The method of healing a skin wound according to claim 2, wherein the polypeptide has a concentration of from about 10 µg/ml to about 3 mg/ml in said pharmaceutical medium.

4. The method of healing a skin wound according to claim 2, wherein the polypeptide has a concentration of from about 30 µg/ml to about 500 µg/ml in said pharmaceutical medium.

5. The method of healing a skin wound according to claim 2, wherein the pharmaceutical composition is applied to the wound about every 6 to about every 72 hours.

6. A method of healing a skin wound comprising contacting the skin wound with an effective amount of a pharmaceutical composition comprising a polypeptide wherein the polypeptide consists of an amino acid sequence of human hsp90a peptide from amino acids 236 to 350.

7. The method of healing a skin wound according to claim 6, wherein the pharmaceutical composition further comprises a pharmaceutical medium to carry the polypeptide, wherein the pharmaceutical medium is selected from the group consisting of an aqueous solution, suspension, dispersion, salve, ointment, gel, cream, lotion, spray or paste.

8. The method of healing a skin wound according to claim 7, wherein the polypeptide has a concentration of from about 10 µg/ml to about 3 mg/ml in said pharmaceutical medium.

9. The method of healing a skin wound according to claim 7, wherein the polypeptide has a concentration of from about 30 µg/ml to about 500 µg/ml in said pharmaceutical medium.

10. The method of healing a skin wound according to claim 7, wherein the composition is applied to the wound about every 24 to about every 48 hours.

11. A method of healing a skin wound comprising contacting the skin wound with an effective amount of a pharmaceutical composition consisting of a polypeptide, wherein the polypeptide consists of amino acid sequence SDEEEEKKDGDKKKKKKIKEKYIDQEE (SEQ. ID NO. 2).

12. The method of healing a skin wound according to claim 11, wherein the pharmaceutical composition further comprises a pharmaceutical medium to carry the polypeptide, wherein the pharmaceutical medium is selected from the group consisting of an aqueous solution, suspension, dispersion, salve, ointment, gel, cream, lotion, spray or paste.

13. The method of healing a skin wound according to claim 12, wherein the polypeptide has a concentration of from about 10 µg/ml to about 3 mg/ml in said pharmaceutical medium.

14. The method of healing a skin wound according to claim 12, wherein the polypeptide has a concentration of from about 30 µg/ml to about 500 µg/ml in said pharmaceutical medium.

15. The method of healing a skin wound according to claim 12, wherein the composition is applied to the wound about every 24 to about every 48 hours.

* * * * *

```
SEQUENCE LISTING

<160> NUMBER OF SEQ ID NOS: 2

<210> SEQ ID NO 1
<211> LENGTH: 54
<212> TYPE: PRT
<213> ORGANISM: Homo sapiens

<400> SEQUENCE: 1

Glu Glu Lys Glu Asp Lys Glu Glu Lys Glu Lys Glu Glu Lys Glu
1               5                   10                  15

Ser Glu Asp Lys Pro Glu Ile Glu Asp Val Gly Ser Asp Glu Glu
            20                  25                  30

Glu Lys Lys Asp Gly Asp Lys Lys Lys Lys Lys Ile Lys Glu Lys
        35                  40                  45

Tyr Ile Asp Gln Glu Glu
    50

<210> SEQ ID NO 2
<211> LENGTH: 27
<212> TYPE: PRT
<213> ORGANISM: Homo sapiens

<400> SEQUENCE: 2

Ser Asp Glu Glu Glu Glu Lys Lys Asp Gly Asp Lys Lys Lys Lys
1               5                   10                  15

Lys Ile Lys Glu Lys Tyr Ile Asp Gln Glu Glu
            20                  25
```